United States Patent [19]

Webb et al.

[11] Patent Number: 4,631,346
[45] Date of Patent: Dec. 23, 1986

[54] SILYL CARBAMATES AND THEIR USE IN THE PREPARATION OF BIS (AMINOALKYL) DISILOXANES

[75] Inventors: Jimmy L. Webb, Ballston Lake; Cathryn E. Olsen, Ballston Spa, both of N.Y.

[73] Assignee: General Electric Company, Schenectady, N.Y.

[21] Appl. No.: 768,255

[22] Filed: Aug. 22, 1985

Related U.S. Application Data

[63] Continuation-in-part of Ser. No. 707,630, Mar. 4, 1985, abandoned.

[51] Int. Cl.[4] ............................ C07F 7/08; C07F 7/10
[52] U.S. Cl. ..................................... 556/420; 556/425
[58] Field of Search ................................ 556/420, 425

[56] References Cited

U.S. PATENT DOCUMENTS 4,160,775  7/1979  Schilling .................... 556/420 X
4,400,526  8/1983  Kanner et al.
4,496,754  1/1985  Kanner et al.

Primary Examiner—Paul F. Shaver
Attorney, Agent, or Firm—William H. Pittman; James C. Davis, Jr.; James Magee, Jr.

[57] ABSTRACT

Silyl carbamates are prepared by reacting carbon dioxide with a silazane composition such as 2-methyl-2-sila-3-aza-5-hexene. The silyl carbamates may be converted to symmetrical bis(aminoalkyl)disiloxanes by hydrosilation followed by hydrolysis.

20 Claims, 7 Drawing Figures

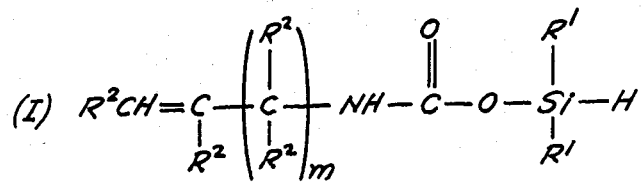
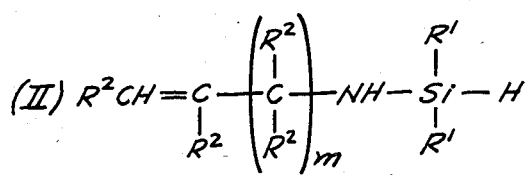
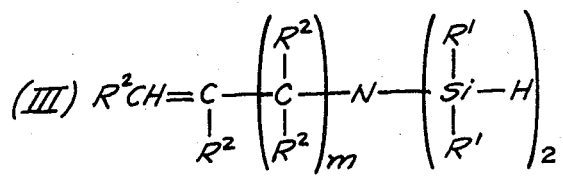
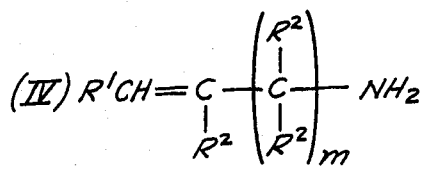
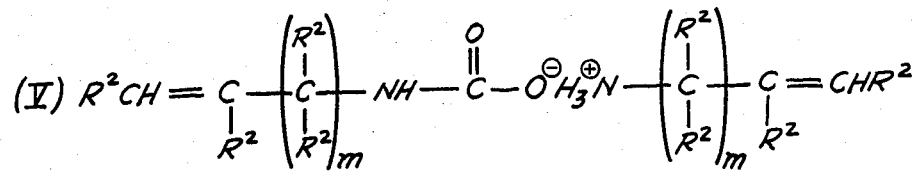
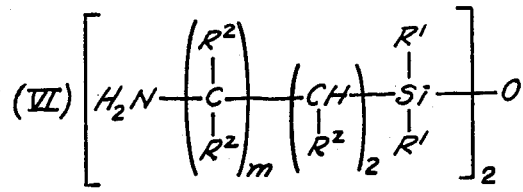
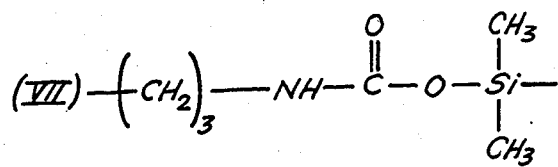

SILYL CARBAMATES AND THEIR USE IN THE PREPARATION OF BIS (AMINOALKYL) DISILOXANES

This application is a continuation-in-part of copending application Ser. No. 707,630, filed Mar. 4, 1985, now abandoned. The entire disclosure of said application is incorporated by reference herein.

This invention relates to the novel silyl carbamates, a method for their preparation and a method for converting them to symmetrical bis(aminoalkyl)disiloxanes.

Bis(aminoalkyl)disiloxanes are useful in many applications including the preparation of polyimides, especially polyetherimides such as those prepared by reaction of diamines with such dianhydrides as 2,2-bis[4-(3,4-dicarboxyphenoxy)phenyl]propane dianhydride ("bisphenol A dianhydride"). A particularly valuable bis(aminoalkyl)disiloxane used for this purpose is 1,9-diamino-4,4,6,6-tetramethyl-5-oxa-4,6-disilanonane, also known as bis(3-aminopropyl)tetramethyldisiloxane and bis(γ-aminopropyl(tetramethyldisiloxane. Commercial utilization of these compounds, however, has been inhibited by the lack of convenient methods for their preparation on a large scale. Previous methods for their preparation have involved a large number of complex and expensive reactions and/or processing steps.

Copending, commonly owned application Ser. No. 691,293, filed Jan. 14, 1985, describes a method for the preparation of bis(aminoalkyl)disiloxanes from acyclic olefinic silazanes by hydrosilation followed by hydrolysis. The products, however, are frequently mixtures of isomers. For example, the substantially pure monosilazane 2-methyl-2-sila-3-aza-5-hexene can be converted to substantially pure 1,9-diamino-4,4,6,6-tetramethyl-5-oxa-4,6-disilanonane; but the monosilazane is ordinarily obtained in admixture with the disilazane 2-methyl-3-dimethylsilyl-2-sila-3-aza-5-hexene, and hydrosilation-hydrolysis of such mixtures yields a mixture of 1,9-diamino-4,4,6,6-tetramethyl-5-oxa-4,6-disilanonane with its isomers 1,8-diamino-2,3,3,5,5-pentamethyl-4-oxa-3,5-disilaoctane (which is unsymmetrical) and 1,7-diamino-2,3,3,5,5-6-hexamethyl-4-oxa-3,5-disilaheptane. Therefore, there is still an interest in developing methods for preparing substantially isomer-free symmetrical bis(aminoalkyl)disiloxanes.

A principal object of the present invention, therefore, is to provide a new method for the preparation of symmetrical bis(aminoalkyl)disiloxanes.

A further object is to prepare said bis(aminoalkyl)-disiloxanes substantially free from isomers thereof.

A further object is to provide a preparative method which is convenient and relatively inexpensive.

A still further object is to provide novel chemical intermediates which are useful in said method, and a method for their preparation.

Other objects will in part be obvious and will in part appear hereinafter.

In one of its aspects, the present invention is directed to silyl carbamates having formula I in the drawings, wherein $R^1$ is a $C_{1-4}$ primary or secondary alkyl radical, phenyl or substituted phenyl; each $R^2$ is independently hydrogen, a $C_{1-4}$ primary or secondary alkyl radical, phenyl or substituted phenyl; and m is from 1 to about 20.

As is apparent from formula I, the silyl carbamates of this invention are characterized by the presence of a terminal olefinic bond in the organic group attached to nitrogen. The $R^1$ values therein may be phenyl radicals; substituted phenyl radicals such as tolyl, chlorophenyl, carbomethoxyphenyl or cyanophenyl; or (preferably) $C_{1-4}$ primary or secondary alkyl radicals such as methyl, ethyl, 1-propyl, 2-propyl, 1-butyl, 2-butyl and 2-methyl-1-propyl. Methyl and ethyl radicals, especially methyl, are particularly preferred.

The $R^2$ values are usually all hydrogen. Any of them may, however, be phenyl, substituted phenyl or $C_{1-4}$ primary or secondary alkyl radicals such as those described hereinabove with respect to $R^1$, with the same preferences. It should be noted that the present invention contemplates the use of compounds wherein all $R^2$ values are the same, as well as compounds wherein they are all different. This includes compounds in which m is up to about 20 and all of the $R^2$ substituents on the resulting alkylene radical are different. The value of m is usually 1 or 2 and preferably 1.

The silyl carbamates of this invention may be prepared by carbonating a silazane composition comprising at least one of (1) a monosilazane of formula II in the drawings and (2) a mixture of a disilazane of formula III in the drawing and an amine of formula IV in the drawings; that is, by reacting said composition with carbon dioxide. The silazane composition may be prepared by known methods such as the reaction of an olefinic amine of formula IV with a chlorosilane of the formula $(R^1)_2SiHCl$ in the presence of an acid acceptor such as excess olefinic amine, as disclosed, for example, in Example 12 of U.S. Pat. No. 3,642,854, the disclosure of which is incorporated by reference herein. Suitable olefinic amines include allylamine (which is preferred), methallylamine and 3-butenylamine. The preferred chlorosilane is dimethylchlorosilane.

The product of the olefinic amine-chlorosilane reaction is the monosilazane of formula II, the corresponding disilazane of formula III, or a mixture thereof, depending on various factors such as the molar ratio of the reactants. While no part of the present invention is dependent on any particular theory of reaction, it is believed that the monosilazane undergoes a disproportionation reaction upon standing, yielding the disilazane and the olefinic amine in equimolar amounts. The disproportionation reaction is apparently an equilibrium reaction, and an important feature of the present invention is the fact that it is immaterial whether or not said reaction takes place. This circumstance is described more fully hereinafter.

Carbonation may be accomplished by passing carbon dioxide into the silazane composition at a temperature of about 25°–125° C. Elevated temperatures, usually at least about 50° C., are usually required for carbonating disilazanes; monosilazanes may frequently be carbonated at room temperature. If a monosilazane-disilazane mixture is used, the exothermic monosilazane-carbon dioxide reaction may increase the temperature sufficiently to initiate disilazane carbonation. In general, temperatures up to about 100° C. are preferred.

It is generally advantageous to employ a solvent for the silazane composition. Typical solvents are aliphatic hydrocarbons such as n-hexane and petroleum naphtha, aromatic hydrocarbons such as toluene and xylene, ethers such as tetrahydrofuran and dioxane, and aprotic polar solvents such as dimethyl sulfoxide.

The carbonation of trialkylsilazanes to the corresponding silyl carbamates is known in the art. Reference is made, for example, to Japanese Kokai No. 79/119418; Zoeckler et al., J. Org. Chem., 48, 2539–2543 (1983); and Breederveld, *Rec. trav. chim.*, 81, 276–278 (1962). However, these publications relate only to the carbonation of silazanes containing three methyl groups attached to silicon. Moreover, the Breederveld method is applicable only to dialkylamino compounds and the other two require catalysts such as transition metal chlorides, ruthenium carbonyl or rhodium carbonyl. According to the present invention, on the other hand, carbonation of compounds containing only two hydrocarbon substituents on silicon and one on nitrogen is easily accomplished in the absence of catalysts. It is generally mildly exothermic and proceeds with facility at the above-described temperatures.

It is also within the scope of the invention to carbonate a mixture of the monosilazane with the corresponding disilazane and olefinic amine, the latter two compounds generally being present in approximately equimolar amounts. Again disclaiming basis on any reaction theory, it is believed that an intermediate species is an ammonium carbamate of formula V in the drawing which can in turn react (through the carbamate anion) either with monosilazane to form silyl carbamate and olefinic amine, or with disilazane to form silyl carbamate, monosilazane and olefinic amine with the monosilazane in turn reacting with more carbon dioxide. The overall result is that any free olefinic amine plays a catalytic role in the carbonation sequence. In any event, the desired symmetrical bis(aminoalkyl)-disiloxane is the only final product obtained irrespective of the presence of disilazane and olefinic amine in the silazane composition.

The preparation of the silyl carbamates of this invention is illustrated by the following examples. All parts are by weight.

EXAMPLE 1

A silazane composition was prepared by the reaction of dimethylchlorosilane with allylamine to produce 2-methyl-2-sila-3-aza-5-hexene. Upon storage, disproportionation occurred and the product actually used contained 50 mole percent of the monosilazane and 25 mole percent each of allylamine and 2-methyl-2-sila-3-dimethylsilyl-3-aza-5-hexene.

A solution of 40 parts of the silazane composition in 40 parts of toluene was heated to 80°–85° C., with stirring, as carbon dioxide was passed in under the surface. A positive pressure of about 1–3 inches of toluene was maintained; under these conditions, there was no net escape of gas from the reaction vessel. An exothermic reaction occurred, after which the temperature was raised to 110° C. The reaction was monitored by vapor phase chromatography and mass spectroscopy, which showed the formation of the desired dimethylsilyl allylcarbamate. Carbon dioxide addition was discontinued when no further reactants were detected.

EXAMPLE 2

The procedure of Example 1 was repeated, using a silazane composition comprising about 74% 2-methyl-2-sila-3-aza-5-hexene and about 18% 2-methyl-2-sila-3-dimethylsilyl-3-aza-5-hexene. A substantially identical product was obtained.

EXAMPLE 3

The procedure of Example 1 was repeated, using substantially pure, freshly prepared 2-methyl-2-sila-3-aza-5-hexene. A substantially identical product was obtained.

EXAMPLE 4

A mixture of equimolar proportions of 2-methyl-2-sila-3-dimethylsilyl-3-aza-5-hexene and allylamine was charged to a carefully dried round-bottomed flask fitted with a thermometer, sintered glass tube for gas introduction and condenser, maintained under dry conditions. A tube sealed in the top of the condenser passed into a cylinder of toluene to provide back pressure.

The mixture was heated to 50° C. and dry carbon dioxide was bubbled in at a rate which just balanced the back pressure so that all the carbon dioxide was absorbed. An exothermic reaction occurred which caused the temperature of the reaction mixture to increase to 80° C. When absorption of carbon dioxide had ceased, the mixture was analyzed by gas chromatography and was found to comprise dimethylsilyl allylcarbamate of high purity.

The silyl carbamates of this invention are useful as intermediates in the preparation of symmetrical bis-(aminoalkyl)disiloxanes. Accordingly, another aspect of the present invention is a method for preparing a symmetrical bis(aminoalkyl)disiloxane of formula VI in the drawing, wherein $R^1$, $R^2$ and m are as previously defined, which comprises (A) contacting a silyl carbamate of formula I with a hydrosilation catalyst to form an intermediate, and (B) hydrolyzing said intermediate.

Hydrosilation catalysts useful in step A are those known in the art. They are typically platinum catalysts in which the platinum may be present in elemental or chemically combined (i.e., divalent or tetravalent) form. Illustrative hydrosilation catalysts are platinum supported on substantially inert substrates such as carbon, aluminum or silica gel; platinum compounds such as $PtCl_4$, $Na_2PtCl_4$, $K_2PtCl_4$, $H_2PtCl_6$, $PtCl_2(CH_3CN)_2$ and alkylplatinum halides; and siloxyorganosulfur-platinum or aluminoxyorganosulfur-platinum compositions of the type disclosed in U.S. Pat. No. 4,503,160, the disclosure of which is incorporated by reference herein.

In many instances, the hydrosilation catalyst is preferably formed by the reaction of a platinum compound with at least one olefinic siloxane, as disclosed in the following U.S. patents:

| | |
|---|---|
| 3,419,593 | 3,814,730 |
| 3,715,334 | 4,288,345. |
| 3,775,452 | |

The disclosures of these patents are incorporated by reference herein. Particularly useful as the reaction products of platinum compounds, especially chloroplatinic acid and hydrates thereof, with 3,3,5,5-tetramethyl-3,5-disila-4-oxa-1,6-heptadiene. The amount of hydrosilation catalyst used is usually such as to provide an amount of platinum equal to about 10–400 ppm. (by weight) based on the olefinic amine.

Step A may be conveniently conducted by heating the mixture of the silyl carbamate and hydrosilation catalyst at a temperature in the range of about 75°–125° C., preferably in a substantially inert organic solvent such as those listed hereinabove.

The molecular structure of the intermediate formed in step A is not known with certainty. It appears to be polymeric. Relating specifically to the hydrosilation product of dimethylsilylallyl carbamate, there is evidence that it comprises structural units having formula VII in the drawing. However, the molecular structure of the intermediate is not a limiting feature of the invention.

In step B, the intermediate formed in step A is hydrolyzed. Hydrolysis may be conveniently and simply effected by merely adding water to the intermediate, which is most often maintained in solution in the solvent previously used. The reaction is exothermic and is accompanied by the evolution of carbon dioxide. It is usually preferred to add the water gradually at a temperature within the range of about 80°–110° C.

In general, an excess of water is employed, typically about a 25–100% excess. When all the water has been added, the mixture may be heated to a temperature within the range of about 75°–100° C. to drive the reaction to completion. The desired symmetrical bis(aminoalkyl)disiloxane may then be recovered by conventional methods such as distillation or crystallization.

It is sometimes found that the symmetrical bis(aminoalkyl)disiloxane product obtained by the method of this invention contains minor but substantial amounts of higher bis(aminoalkyl)siloxanes, such as the trisiloxane and tetrasiloxane. The presence of such higher siloxanes is generally not detrimental to the known utilities of the bis(aminoalkyl)disiloxanes. This is particularly true when the product is to be used in the preparation of polyimides, since a preliminary step in said preparation is frequently the equilibration of the diamine with such materials as octamethylcyclotetrasiloxane to increase the number of siloxane units therein.

The method of this invention for the preparation of symmetrical bis(aminoalkyl)disiloxanes is illustrated by the following examples.

EXAMPLE 5

The silyl carbamate solution of Example 1 was combined with 1 ml. of a hydrosilation catalyst prepared from chloroplatinic acid and 3,3,5,5-tetramethyl-3,5-disila-4-oxa-1,6-heptadiene by the method disclosed in Example 10 of U.S. Pat. No. 3,814,730, said catalyst containing 5% platinum. The resulting solution contained platinum in the amount of 200 ppm. based on silyl carbamate. The mixture was heated slowly, with stirring, whereupon an exothermic reaction occurred and the temperature rose about 20° C. When the exotherm had subsided, the mixture was heated under reflux for 8 hours. Analysis then showed that all the silyl carbamate had reacted.

The mixture was cooled and a 50% stoichiometric excess of water was added dropwise, with stirring, whereupon an exothermic reaction occurred. The rate of water addition was regulated so as to maintain a reaction temperature of about 50° C. When the exotherm had subsided, the mixture was heated under reflux for 15 hours. The toluene and solvent were then removed by distillation and the product was distilled; the desired 1,9-diamino-4,4,6,6-tetramethyl-5-oxa-4,6-disilanonane was recovered at 100° C./1 torr. The yield was 84% of theoretical, and the product contained about 20% trisiloxane and about 5% tetrasiloxane.

EXAMPLE 6

The procedure of Example 5 was repeated, using as a starting material the silyl carbamate composition of Example 2. The yield of 1,9-diamino-4,4,6,6-tetramethyl-5-oxa-4,6-disilanonane was 82%, and the product contained about 20% trisiloxane and about 5% tetrasiloxane.

EXAMPLE 7

The procedure of Example 6 was repeated, using the silyl carbamate composition of Example 5. Similar results were obtained.

EXAMPLE 8

The silyl carbamate solution of Example 1 was combined with platinum tetrachloride to provide 200 ppm. of platinum based on silyl carbamate. The mixture was heated slowly, with stirring, whereupon an exothermic reaction occurred and the temperature rose about 20° C. When the exotherm had subsided, the mixture was heated under reflux until analysis showed that all the silyl carbamate had reacted.

The mixture was maintained at 100° C. as a 50% stoichiometric excess of water was added dropwise, with stirring. The mixture was heated at 100° C. for one hour after water addition was complete. The toluene and solvent were then removed by distillation and the product was distilled; the desired 1,9-diamino-4,4,6,6-tetramethyl-5-oxa-4,6-disilanonane was recovered at 100° C./1 torr. The yield was 84.5% of theoretical, and the product contained about 14.6% trisiloxane and 1.6% tetrasiloxane.

EXAMPLES 9–12

The procedure of Example 8 was repeated, using the silyl carbamate composition of Example 4 and various platinum-containing catalysts in substantially equivalent amounts. The relative parameters and results are given in the following table.

| Example | Catalyst | Hydrosilation time, hrs. | % product |
|---|---|---|---|
| 9 | Pt (1% on carbon) | 8 | 68 |
| 10 | $PtCl_2(CH_3CN)_2$ | 4 | 62 |
| 11 | $H_2PtCl_6.6H_2O$ | 4 | 67 |
| 12 | Same as Example 5 | 8 | 76 |

What is claimed is:

1. A silyl carbamate having formula I in the drawings, wherein $R^1$ is a $C_{1-4}$ primary or secondary alkyl radical, phenyl or substituted phenyl; each $R^2$ is independently hydrogen, a $C_{1-4}$ primary or secondary alkyl radical, phenyl or substituted phenyl; and m is from 1 to about 20.

2. A silyl carbamate according to claim 1 wherein m is 1 or 2.

3. A silyl carbamate according to claim 2 wherein each $R^2$ is hydrogen.

4. A silyl carbamate according to claim 3 wherein $R^1$ is methyl.

5. A silyl carbamate according to claim 4 wherein m is 1.

6. A method for preparing a silyl carbamate according to claim 1 which comprises reacting carbon dioxide with a silazane composition comprising at least one of (1) a monosilazane of formula II in the drawing and (2) a mixture of a disilazane of formula III in the drawing and an amine of formula IV in the drawing.

7. A method according to claim 6 wherein m is 1 or 2.

8. A method according to claim 7 wherein carbonation is effected at a temperature within the range of about 25°–125° C. in the absence of catalysts.

9. A method according to claim 8 wherein $R^1$ is methyl and each $R^2$ is hydrogen.

10. A method according to claim 9 wherein the silazane composition is a monosilazane.

11. A method according to claim 9 wherein the silazane composition is a mixture of monosilazane, disilazane and olefinic amine, the latter two being present in substantially equimolar amounts.

12. A method according to claim 9 wherein m is 1.

13. A method for preparing a bis(aminoalkyl)disiloxane having formula VI in the drawing which comprises (A) contacting a silyl carbamate according to claim 1 with a hydrosilation catalyst to form an intermediate, and (B) hydrolyzing said intermediate.

14. A method according to claim 13 wherein m is 1 or 2.

15. A method according to claim 14 wherein the hydrosilation catalyst is formed by the reaction of a platinum compound with at least one olefinic siloxane.

16. A method according to claim 15 wherein step B is conducted by adding an excess of water gradually to the intermediate formed in step A, said intermediate being maintained at a temperature within the range of about 80°–110° C.

17. A method according to claim 16 wherein the hydrosilation catalyst is a reaction product of a platinum compound with 3,3,5,5-tetramethyl-3,5-disila-4-oxa-1,6-heptadiene.

18. A method according to claim 17 wherein the platinum compound is chloroplatinic acid or a hydrate thereof.

19. A method according to claim 18 wherein $R^1$ is methyl and each $R^2$ is hydrogen.

20. A method according to claim 19 wherein m is 1.

* * * * *